(12) United States Patent
Kordić et al.

(10) Patent No.: US 12,258,320 B2
(45) Date of Patent: *Mar. 25, 2025

(54) SOLID STATE FORMS OF MAVACAMTEN AND PROCESS FOR PREPARATION THEREOF

(71) Applicant: Assia Chemical Industries Ltd., Tel Aviv (IL)

(72) Inventors: Lorena Kordić, Rab (HR); Dijana Škalec Šamec, Jastrebarsko (HR)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/610,777

(22) Filed: Mar. 20, 2024

(65) Prior Publication Data

US 2024/0228442 A1 Jul. 11, 2024

Related U.S. Application Data

(63) Continuation of application No. 17/792,754, filed as application No. PCT/US2021/015358 on Jan. 28, 2021.

(60) Provisional application No. 63/008,009, filed on Apr. 10, 2020, provisional application No. 62/980,503, filed on Feb. 24, 2020, provisional application No. 62/966,665, filed on Jan. 28, 2020.

(51) Int. Cl.
*C07D 239/10* (2006.01)

(52) U.S. Cl.
CPC ........ *C07D 239/10* (2013.01); *C07B 2200/13* (2013.01)

(58) Field of Classification Search
CPC ..................... C07D 239/10; C07B 2200/13
See application file for complete search history.

(56) References Cited

U.S. PATENT DOCUMENTS

| | | | |
|---|---|---|---|
| 9,181,200 B2 | 11/2015 | Oslob et al. | |
| 2023/0158027 A1 | 5/2023 | Carlson et al. | |

FOREIGN PATENT DOCUMENTS

| | | |
|---|---|---|
| CN | 112939876 A | 6/2021 |
| IN | 202241029652 A | 12/2023 |
| WO | 2014205223 A1 | 12/2014 |
| WO | 2019028360 A1 | 2/2019 |
| WO | 2021092598 A1 | 5/2021 |
| WO | 2022162701 A1 | 8/2022 |
| WO | 2022189599 A1 | 9/2022 |
| WO | 2023199258 A1 | 10/2023 |

OTHER PUBLICATIONS

Applicant Reply in corresponding European Patent Application No. 21706793.3 Jan. 23,2024, 43 pages.
Applicant Reply in corresponding European Patent Application No. 21706793.3 Mar. 8, 2024, 9 pages.
Caira Mino; "Crystalline Polymorphism of Organic Compounds", Department of Chemistry University, vol. 198, Jan. 1, 1998; pp. 163-208.
EA Office Action in corresponding Eurasian Patent Application No. 202292060 mailed Dec. 12, 2023, together with English language translation, 6 pages.
International Search Report and Written Opinion of the International Searching Authority issued in corresponding application PCT/US2021/015358 mailed May 3, 2021 (14 pages).
Office Action in corresponding European Patent Application No. 21706793.3 mailed Feb. 27, 2024, 3 pages.
Office Action in corresponding European Patent Application No. 21706793.3 mailed Jul. 13, 2023, 4 pages.
Office Action issued in corresponding Eurasian Patent Application No. 202292060/28, mailed Jun. 9, 2023, together with English language translation. 4 pages.
Third Party Observations in corresponding European Patent Application No. 21706793.3 mailed Feb. 20, 2024, 13 pages.
Third Party Observations in corresponding European Patent Application No. 21706793.3 mailed Jun. 27, 2023, 15 pages.
Third Party Observations in corresponding European Patent Application No. 21706793.3 mailed Mar. 13, 2024, 4 pages.
Eurasian Office Action issued in corresponding Eurasian Patent Application No. 202292060/28, mailed Jul. 2, 2024; 4 pages.
Office Action in corresponding Chinese Patent Application No. 202180025380.2 issued Feb. 28, 2024; Machine Translation of pp. 3-6.
Office Action in corresponding Chinese Patent Application No. 202180025380.2 issued Sep. 3, 2024; Machine Translation of pp. 3-6.
Third Party Observations in corresponding European Patent Application No. 21706793.3, mailed Jul. 10, 2024; 141 pages.
JP Office Action issued Oct. 28, 2024 in corresponding Japanese Patent Application No. 2022-546095; 12 pages (includes English Translation).

*Primary Examiner* — Barbara P Badio
(74) *Attorney, Agent, or Firm* — CANTOR COLBURN LLP

(57) ABSTRACT

The present disclosure encompasses solid state forms of Mavacamten, in embodiments crystalline polymorphs of Mavacamten, processes for preparation thereof, and pharmaceutical compositions thereof.

24 Claims, 9 Drawing Sheets

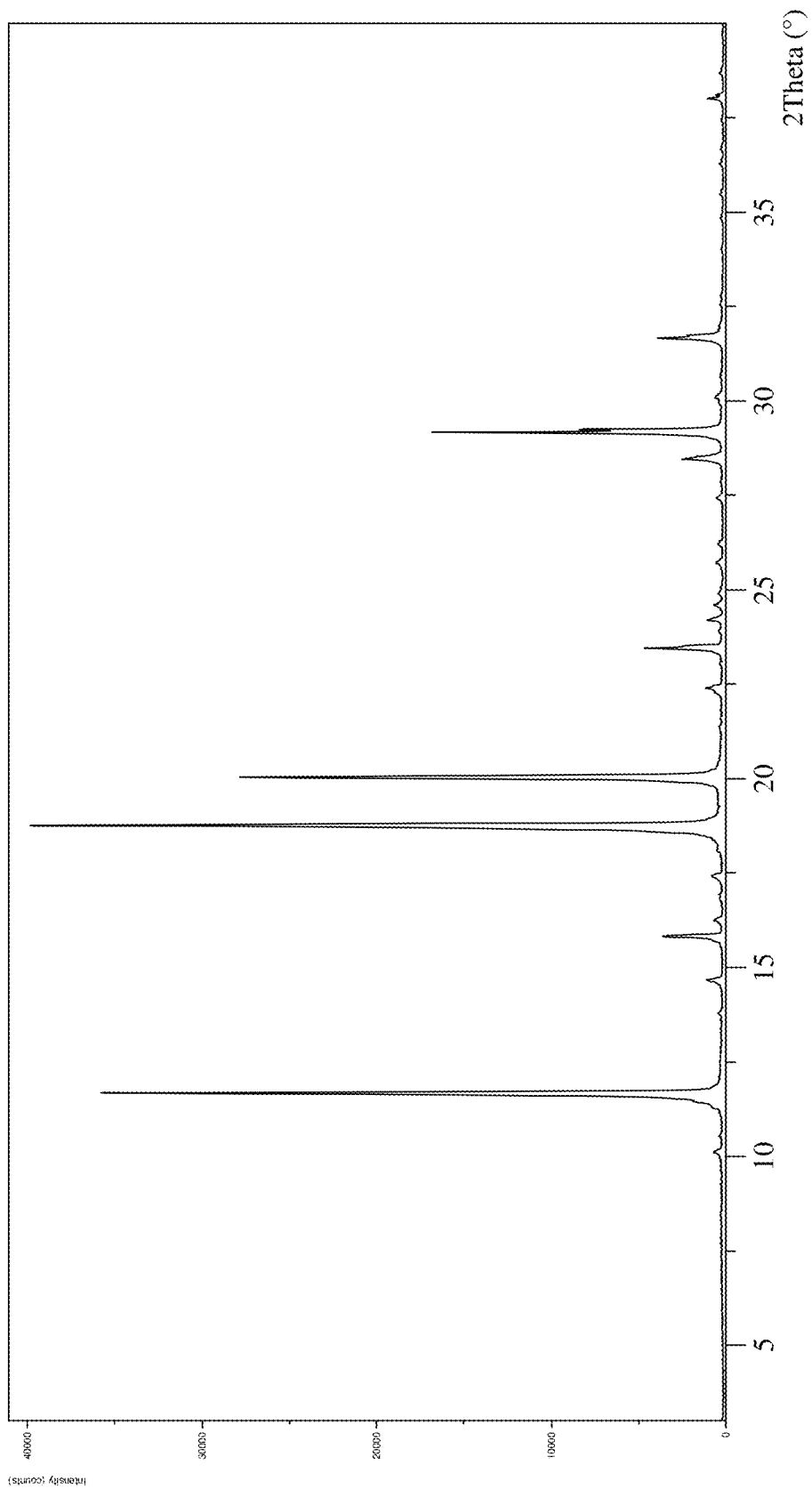
Figure 1: XRPD of Mavacamten Form 1
* Peak at 28.48 belongs to silicon

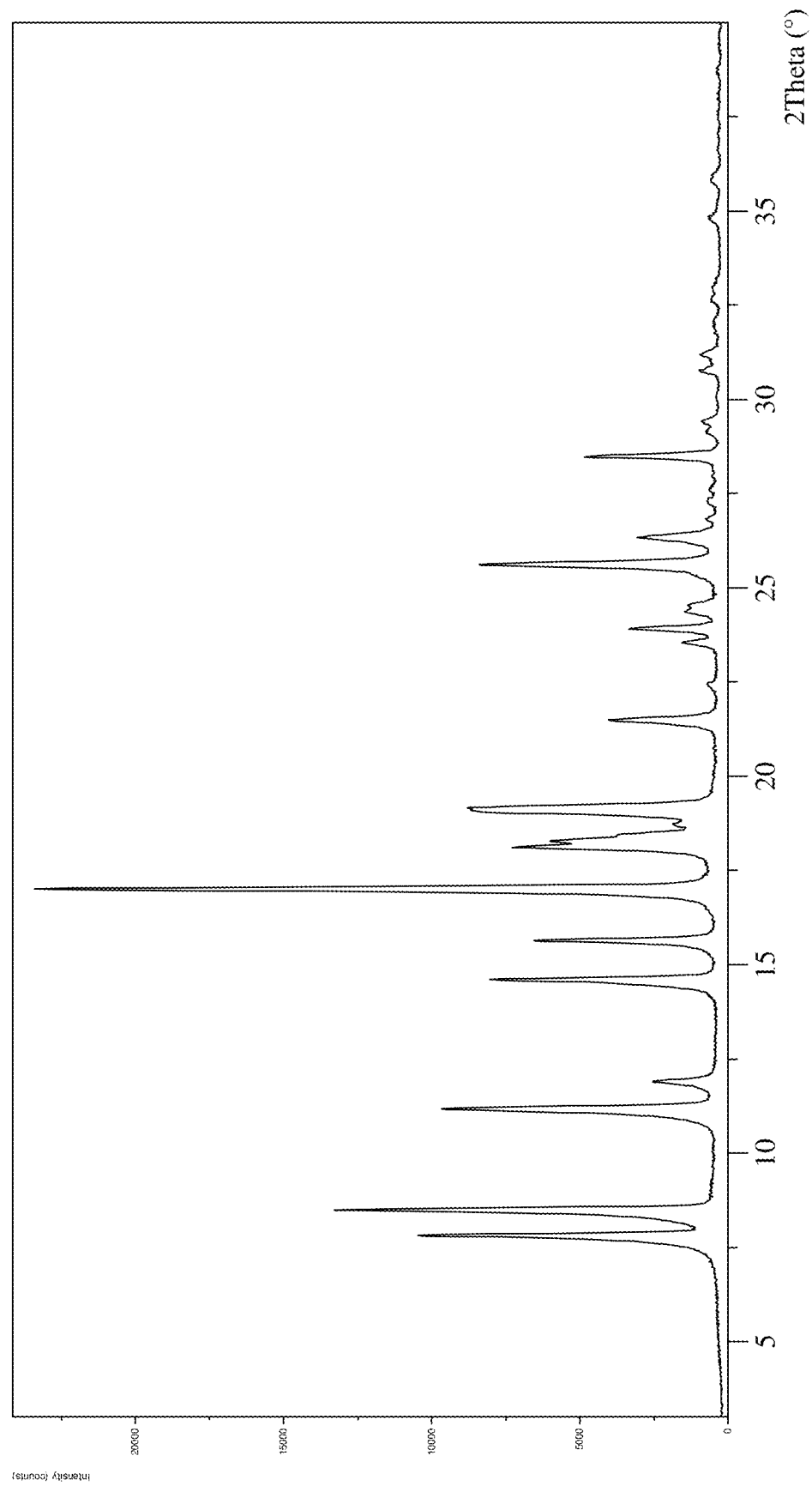
Figure 2: XRPD of Mavacamten Form 2
* Peak at 28.48 belongs to silicon

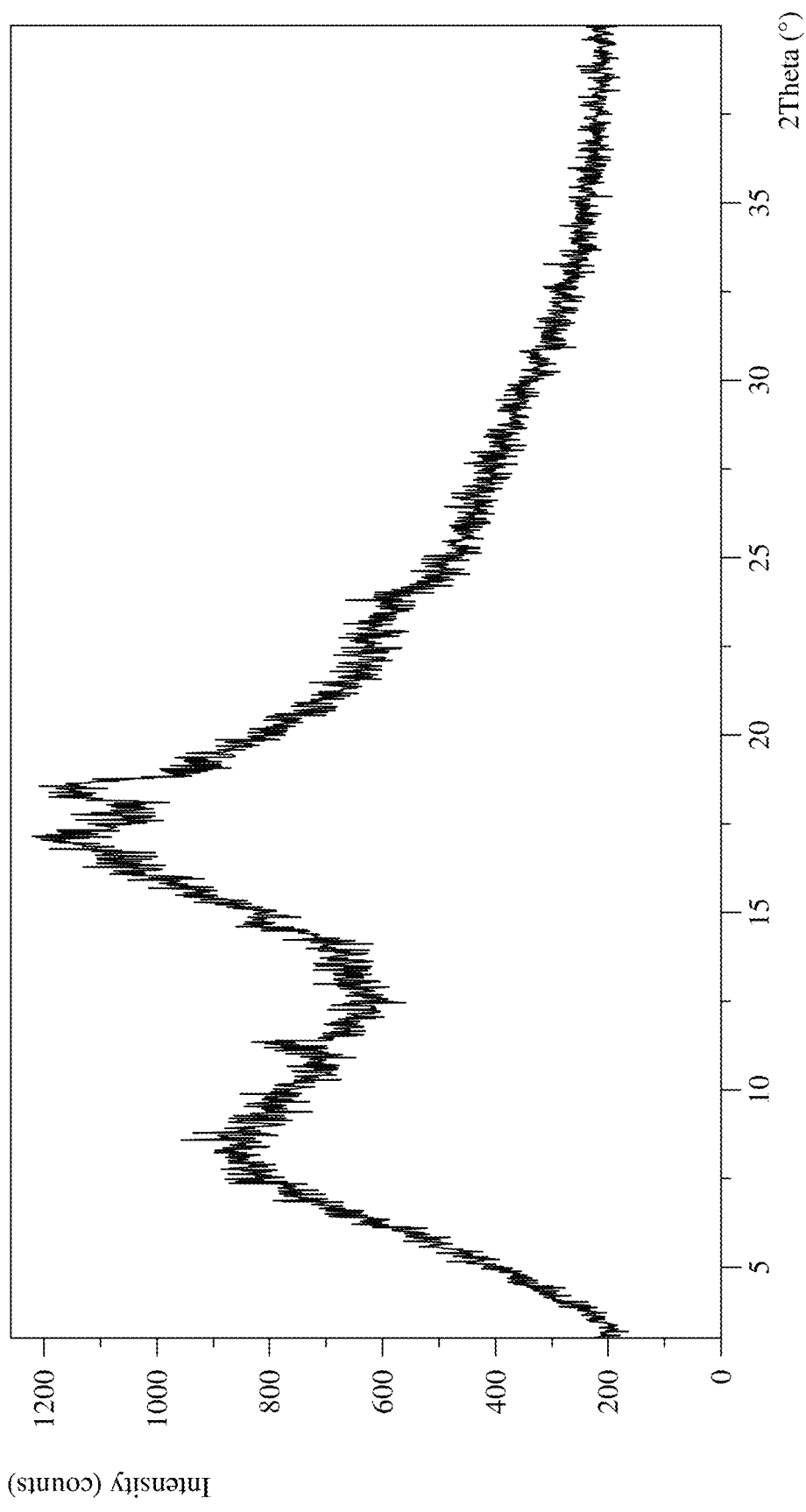
Figure 3: XRPD of Mavacamten amorphous

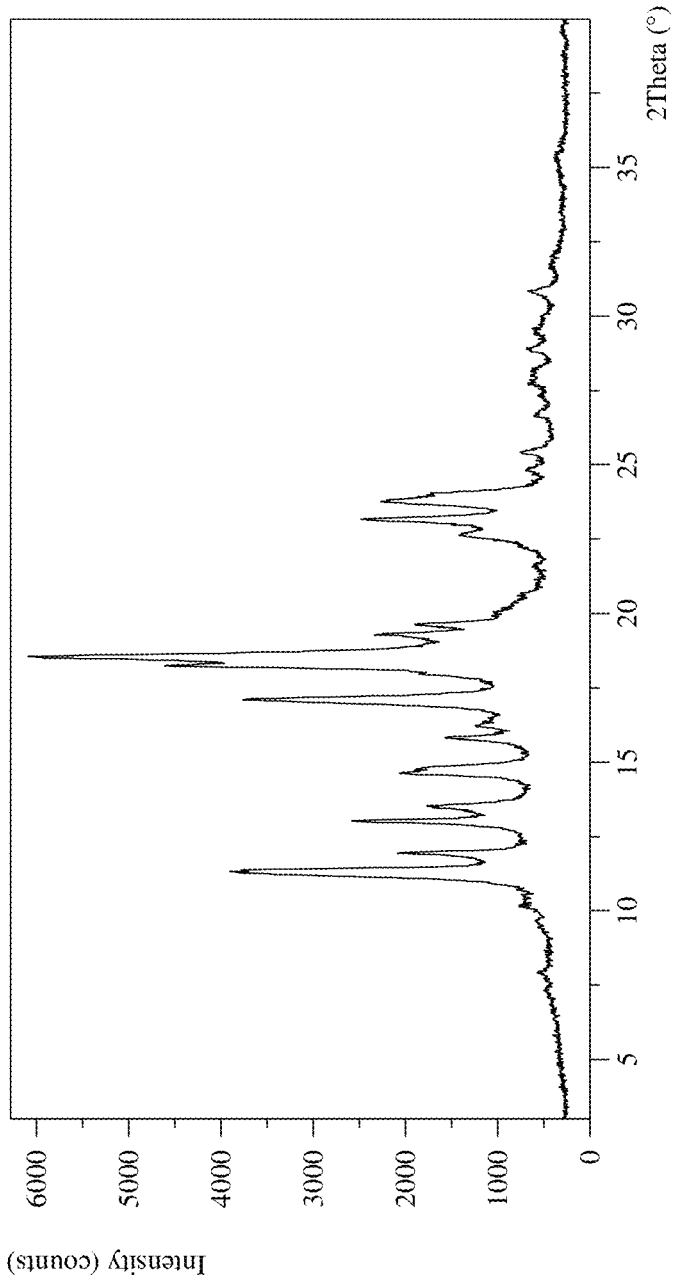
Figure 4: XRPD of Mavacamten Form 4

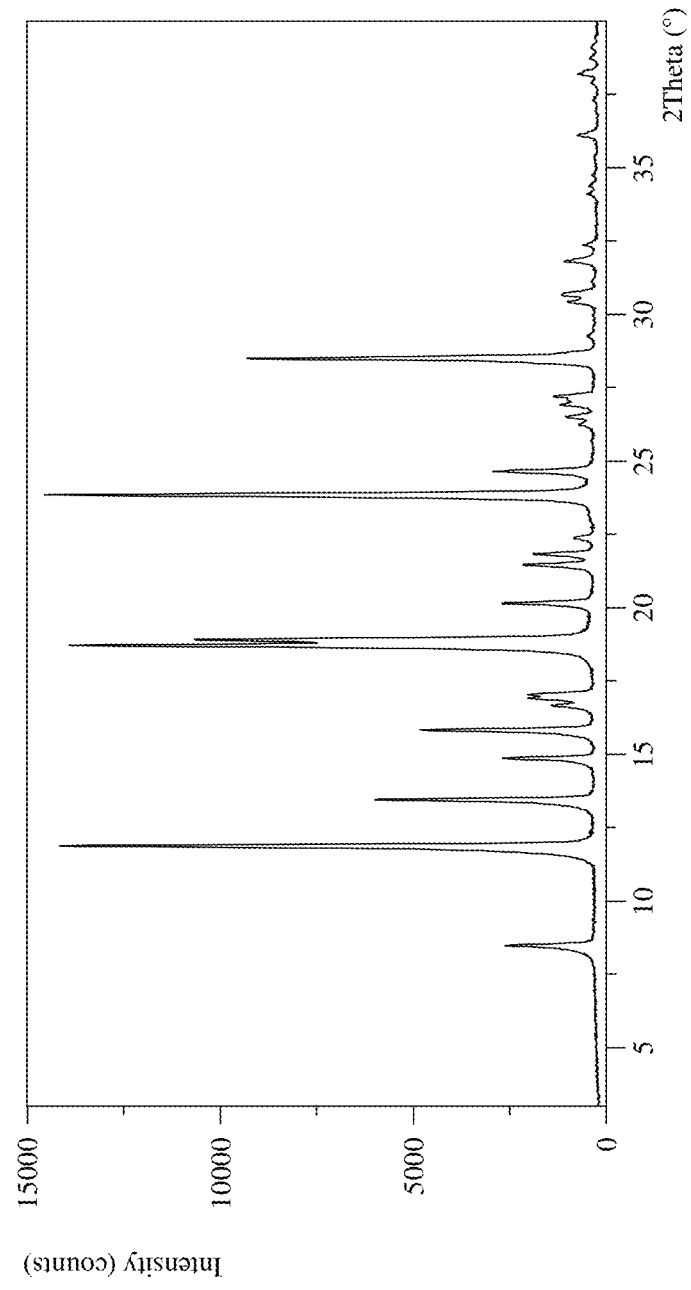
Figure 5: XRPD of Mavacamten Form 5
* Peak at 28.48 belongs to silicon

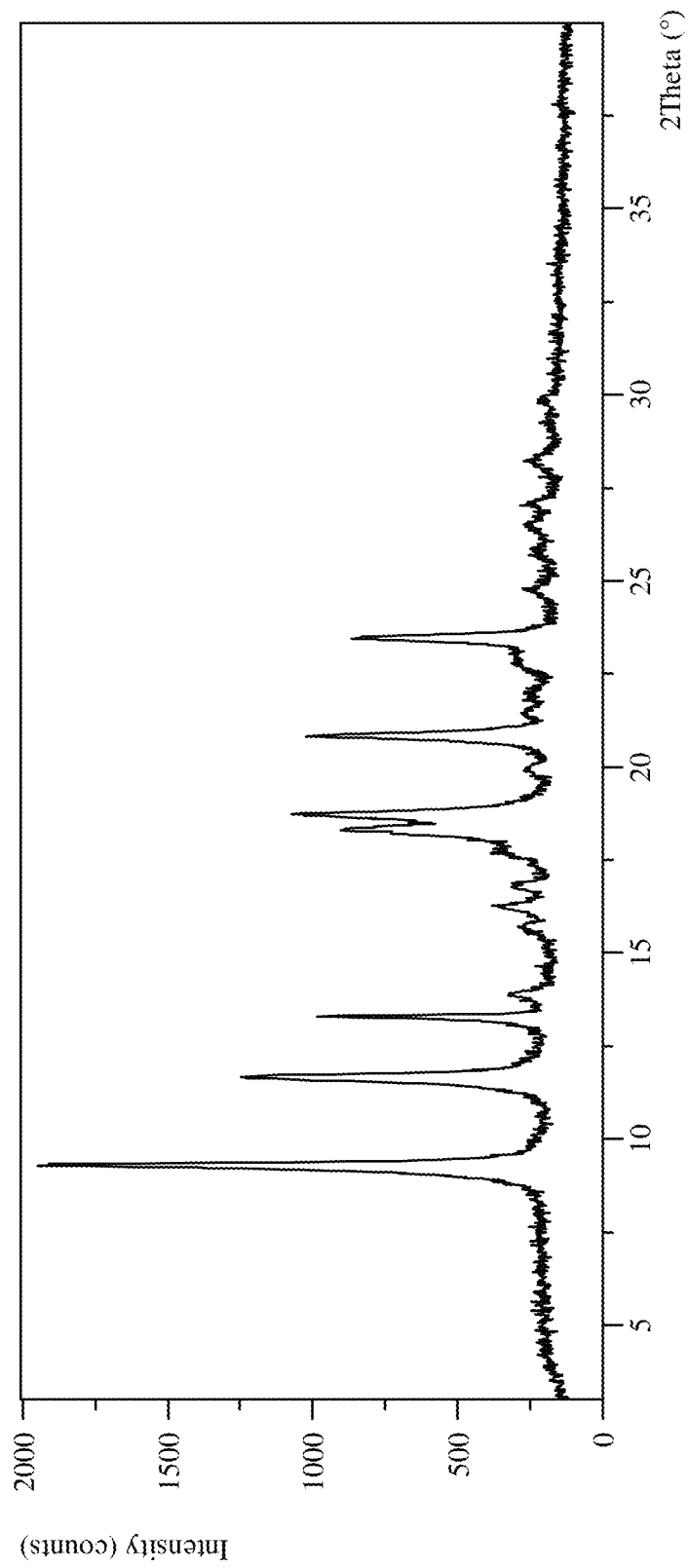
Figure 6: XRPD of Mavacamten Form 6

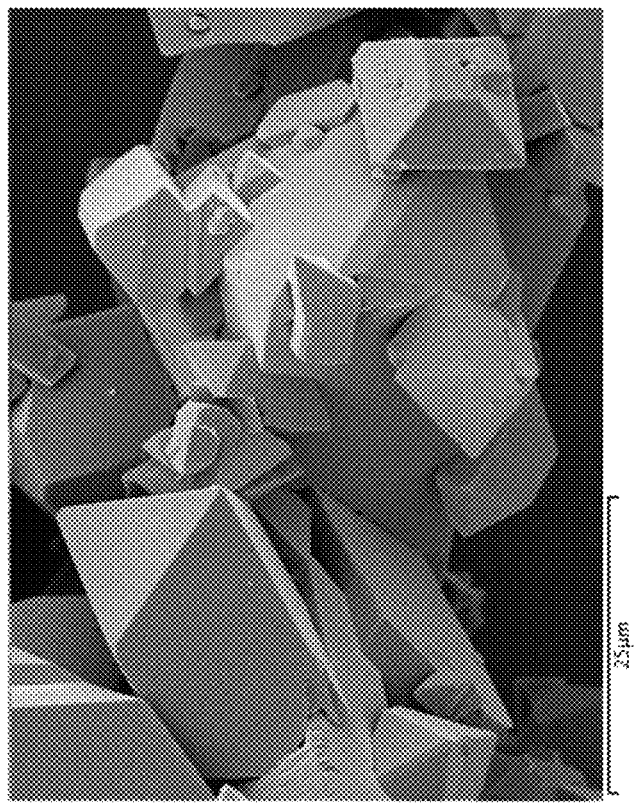
Figure 7: SEM image of Mavacamten Form 1, prepared according to Example 9

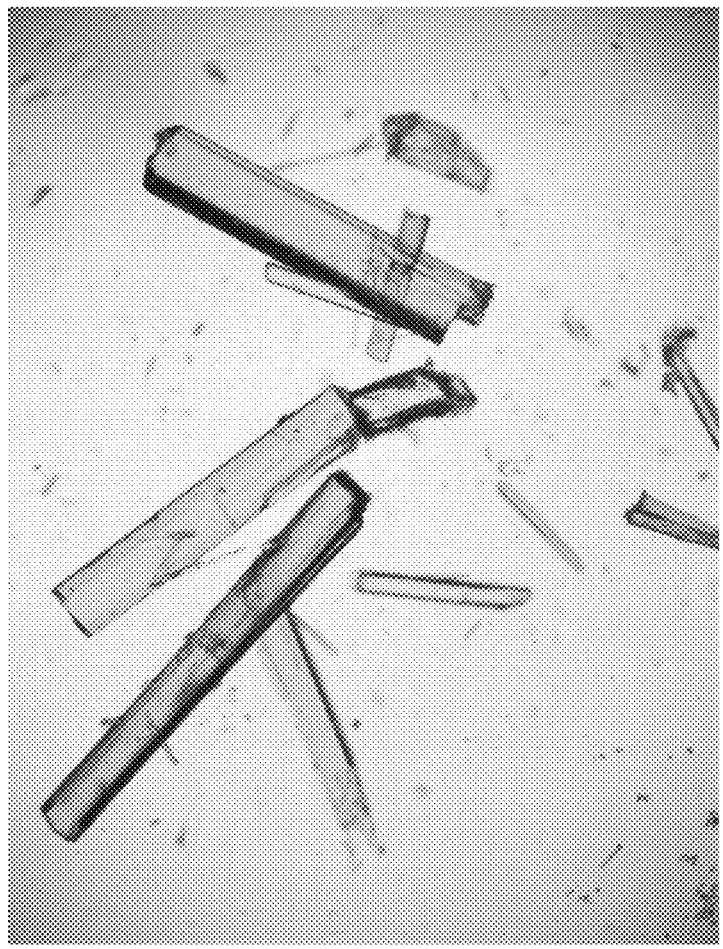
Figure 8: Optical microscopic image of Mavacamten Form 1, prepared according to Example 10

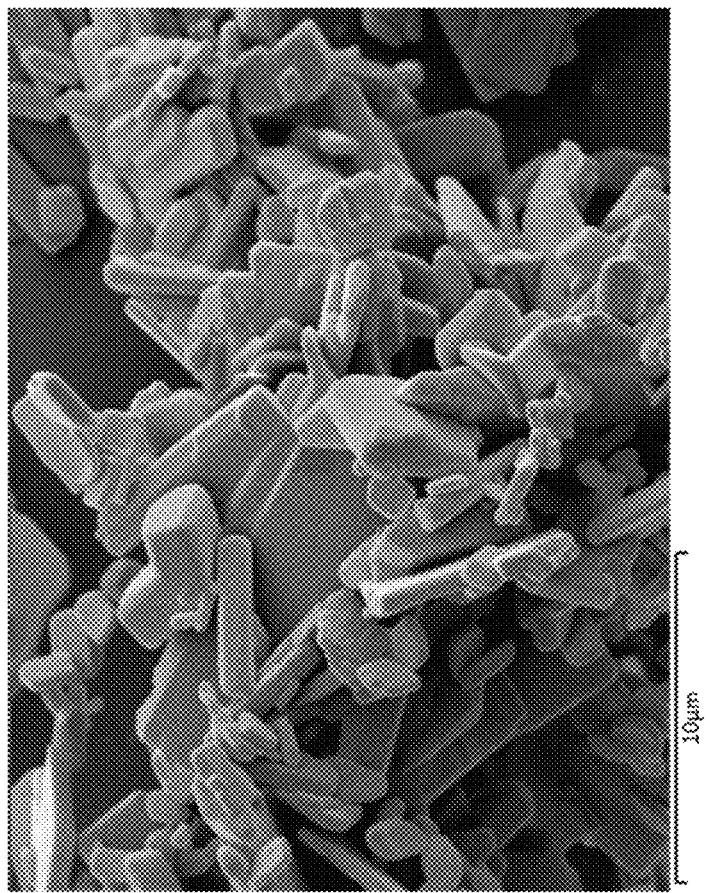
Figure 9: Microscopic image of Mavacamten Form 5, prepared according to Example 11

SOLID STATE FORMS OF MAVACAMTEN AND PROCESS FOR PREPARATION THEREOF

CROSS REFERENCE TO RELATED APPLICATIONS

This application is a continuation application of U.S. patent application Ser. No. 17/792,754, filed Jul. 14, 2022, which is a National Stage of, and claims priority to and the benefit of, International Patent Application No. PCT/US2021/015358, filed Jan. 28, 2021, which, in turn, claims the benefit of and priority to, U.S. Provisional Application No. 62/966,665, filed Jan. 28, 2020; U.S. Provisional Application No. 62/980,503, filed Feb. 24, 2020; and U.S. Provisional Application No. 63/008,009, filed Apr. 10, 2020, the entire disclosures of each of which are incorporated by reference herein.

FIELD OF THE DISCLOSURE

The present disclosure encompasses solid state forms of Mavacamten, in embodiments crystalline polymorphs of Mavacamten, processes for preparation thereof, and pharmaceutical compositions thereof.

BACKGROUND OF THE DISCLOSURE

Mavacamten, 6-{[(1S)-1-phenylethyl]amino}-3-(propan-2-yl)-1,2,3,4-tetrahydropyrimidine-2,4-dione, has the following chemical structure:

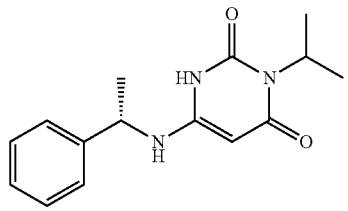 [SMILES: CC(C)n1c(=O)cc(N[C@@H](C)c2ccccc2)[nH]c1=O]

Mavacamten is developed for the treatment of obstructive hypertrophic cardiomyopathy (oHCM).

The compound is described in U.S. Pat. No. 9,181,200.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}$C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Mavacamten.

SUMMARY OF THE DISCLOSURE

The present disclosure provides crystalline polymorphs of Mavacamten, processes for preparation thereof, and pharmaceutical compositions thereof. These crystalline polymorphs can be used to prepare other solid state forms of Mavacamten, Mavacamten salts and their solid state forms.

The present disclosure also provides uses of the said solid state forms of Mavacamten in the preparation of other solid state forms of Mavacamten or salts thereof.

The present disclosure provides crystalline polymorphs of Mavacamten for use in medicine, including for the treatment of cardiovascular disease, especially obstructive hypertrophic cardiomyopathy (oHCM).

The present disclosure also encompasses the use of crystalline polymorphs of Mavacamten of the present disclosure for the preparation of pharmaceutical compositions and/or formulations.

In another aspect, the present disclosure provides pharmaceutical compositions comprising crystalline polymorphs of Mavacamten according to the present disclosure.

The present disclosure includes processes for preparing the above mentioned pharmaceutical compositions. The processes include combining any one or a combination of the crystalline polymorphs of Mavacamten with at least one pharmaceutically acceptable excipient.

The crystalline polymorph of Mavacamten as defined herein and the pharmaceutical compositions or formulations of the crystalline polymorph of Mavacamten may be used as medicaments, such as for the treatment of obstructive hypertrophic cardiomyopathy (oHCM). The present disclosure also provides methods of treating obstructive hypertrophic cardiomyopathy (oHCM), by administering a therapeutically effective amount of any one or a combination of the crystalline polymorphs of Mavacamten of the present disclosure, or at least one of the above pharmaceutical compositions, to a subject suffering from obstructive hypertrophic cardiomyopathy (oHCM), or otherwise in need of the treatment.

The present disclosure also provides uses of crystalline polymorphs of Mavacamten of the present disclosure, or at least one of the above pharmaceutical compositions, for the manufacture of medicaments for treating e.g., obstructive hypertrophic cardiomyopathy.

BRIEF DESCRIPTION OF THE DRAWINGS

FIG. 1 shows a characteristic X-ray powder diffraction pattern (XRPD) of Mavacamten Form 1.

FIG. 2 shows a characteristic XRPD of Mavacamten Form 2.

FIG. 3 shows a characteristic XRPD of Mavacamten amorphous.

FIG. 4 shows a characteristic XRPD of Mavacamten Form 4.

FIG. 5 shows a characteristic XRPD of Mavacamten Form 5.

FIG. 6 shows a characteristic XRPD of Mavacamten Form 6.

FIG. 7 shows SEM image of prism-like morphology of Mavacamten Form 1, prepared according to Example 9.

FIG. 8 shows optical microscopic image of rod-like morphology of Mavacamten Form 1, prepared according to Example 10.

FIG. 9 shows SEM image of plate-like morphology of Mavacamten Form 5, prepared according to Example 11.

DETAILED DESCRIPTION OF THE DISCLOSURE

The present disclosure encompasses solid state forms of Mavacamten, including crystalline polymorphs of Mavacamten, processes for preparation thereof, and pharmaceutical compositions thereof.

Solid state properties of Mavacamten and crystalline polymorphs thereof can be influenced by controlling the conditions under which Mavacamten and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Mavacamten described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Mavacamten. In some embodiments of the disclosure, the described crystalline polymorph of Mavacamten may contain from about 1% to about 20% (w/w), from about 5% to about 20% (w/w), or from about 5% to about 10% (w/w) of one or more other crystalline polymorph of the same Mavacamten.

Depending on which other crystalline polymorphs a comparison is made, the crystalline polymorphs of Mavacamten of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Mavacamten referred to herein as being characterized by graphical data "as depicted in" or "as substantially depicted in" a Figure will thus be understood to include any crystal forms of Mavacamten characterized with the graphical data having such small variations, as are well known to the skilled person, in comparison with the Figure.

As used herein, and unless stated otherwise, the term "anhydrous" in relation to crystalline forms of Mavacamten, relates to a crystalline form of Mavacamten which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to crystalline polymorph of Mavacamten of the present disclosure corresponds to a crystalline polymorph of Mavacamten that is physically separated from the reaction mixture in which it is formed.

As used herein, unless stated otherwise, the XRPD measurements are taken using copper Kα radiation wavelength 1.5418 Å. XRPD peaks reported herein are measured using Cuk α radiation, λ=1.5418 Å, typically at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° ° C. to about 30° ° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes a crystalline polymorph of Mavacamten, designated Form 1. The crystalline Form 1 of Mavacamten may be characterized by data selected from one or more of the following: an X-ray powder diffraction pattern substantially as depicted in FIG. 1; an X-ray powder diffraction pattern having peaks at 11.7, 16.3, 18.7, 20.0 and 23.4 degrees 2-theta±0.2 degrees 2-theta; and combinations of these data.

Crystalline Form 1 of Mavacamten may be further characterized by an X-ray powder diffraction pattern having peaks at 11.7, 16.3, 18.7, 20.0 and 23.4 degrees 2-theta±0.2 degrees 2-theta, and also having any one, two or three additional peaks selected from 17.4, 29.1 and 31.6 degrees 2-theta±0.2 degrees 2-theta.

In one embodiment of the present disclosure, crystalline Form 1 of Mavacamten is isolated.

Crystalline Form 1 of Mavacamten may be anhydrous.

In other embodiment, Crystalline Form 1 of Mavacamten may be characterized by the following cell parameters:

| Space group | Cell lengths/Å | Cell angles |
|---|---|---|
| P2$_1$2$_1$2$_1$ | a = 9.444(3) | α = 90 |
| | b = 12.1038(19) | β = 90 |
| | c = 12.664(2) | γ = 90 |

In some embodiments of the present invention, the crystalline Form 1 of Mavacamten, as defined according to any aspect or embodiment described herein, may be provided in a particular morphology. In particular, the crystalline Form 1 may comprise particles having prism-like morphology or rod-like morphology. Crystalline Form 1 having the morphology as described herein provides advantageous processing characteristics and/or stability due to particles having uniform morphology.

In a further embodiment, crystalline Form 1 of Mavacamten according to the present invention is stable when exposed to high temperatures and high relative humidity.

The present invention also provides a process for preparing Form 1 of Mavacamten. The process comprising:

providing Mavacamten in an organic solvent, preferably an alcohol, particularly methanol, 2-butanol, isobutanol, 1-propanol or dimethyformamide;

heating up to reflux temperature; and crystallizing Form 1 either by solvent evaporation under room temperature conditions, or by cooling the solution to about 0° C.; preferably by ice-bath.

In another aspect of the present invention, there is provided a process for preparing a crystalline Form 1 of Mavacamten comprising providing a suspension of Mavacamten in an organic solvent, preferably an ether, more preferably, a cyclic ether, particularly tetrahydrofuran, at reflux temperature and removing the solvent; preferably by solvent evaporation under room temperature conditions.

The present disclosure also provides Form 2 of Mavacamten. The crystalline From 2 of Mavacamten may be characterized by data selected from one or more of the following: an X-ray powder diffraction pattern substantially as depicted in FIG. 2; an X-ray powder diffraction pattern having peaks at 7.8, 8.5, 11.2, 17.0 and 21.5 degrees 2-theta±0.2 degrees 2-theta; and combinations of these data.

Crystalline Form 2 of Mavacamten may be further characterized by an X-ray powder diffraction pattern having peaks at 7.8, 8.5, 11.2, 17.0 and 21.5 degrees 2-theta±0.2 degrees 2-theta, and also having any one, two, three, four or five additional peaks selected from 11.9, 15.6, 23.9, 25.6 and 26.3 degrees 2-theta±0.2 degrees 2-theta.

In one embodiment of the present disclosure, crystalline Form 2 of Mavacamten is isolated.

In a further embodiment, crystalline Form 2 of Mavacamten may be anhydrous.

The present disclosure also includes a crystalline polymorph of Mavacamten, designated Form 4. The crystalline Form 4 of Mavacamten may be characterized by data selected from one or more of the following: an X-ray powder diffraction pattern substantially as depicted in FIG. 4; an X-ray powder diffraction pattern having peaks at 11.4, 13.0, 19.3, 19.7 and 23.2 degrees 2-theta±0.2 degrees 2-theta; and combinations of these data.

Crystalline Form 4 of Mavacamten may be further characterized by an X-ray powder diffraction pattern having peaks at 11.4, 13.0, 19.3, 19.7 and 23.2 degrees 2-theta±0.2 degrees 2-theta, and also having any one, two, three or four additional peaks selected from 12.0, 13.5, 17.1 and 18.6 degrees 2-theta±0.2 degrees 2-theta.

In one embodiment of the present disclosure, crystalline Form 4 of Mavacamten is isolated.

In a further embodiment, crystalline Form 4 of Mavacamten may be anhydrous.

In a further embodiment, crystalline Form 4 of Mavacamten may be characterized by the following cell parameters:

| Space group | Cell lengths/Å | Cell angles |
|---|---|---|
| P2$_1$2$_1$2$_1$ | a = 9.8539(9) | α = 90 |
| | b = 12.6322(10) | β = 90 |
| | c = 24.2808(17) | γ = 90 |

The present disclosure also provides a crystalline polymorph of Mavacamten, designated Form 5. The crystalline Form 5 of Mavacamten may be characterized by data selected from one or more of the following: an X-ray powder diffraction pattern substantially as depicted in FIG. 5; an X-ray powder diffraction pattern having peaks at 13.4, 14.8, 21.8, 23.8 and 24.6 degrees 2-theta±0.2 degrees 2-theta; and combinations of these data.

Crystalline Form 5 of Mavacamten may be further characterized by an X-ray powder diffraction pattern having peaks at 13.4, 14.8, 21.8, 23.8 and 24.6 degrees 2-theta±0.2 degrees 2-theta, and also having any one, two, three or four additional peaks selected from 11.9, 15.8, 18.9 and 20.1 degrees 2-theta±0.2 degrees 2-theta.

In one embodiment of the present disclosure, crystalline Form 5 of Mavacamten is isolated.

In a further embodiment, crystalline Form 5 of Mavacamten may be anhydrous.

In another embodiment, crystalline Form 5 of Mavacamten may be characterized by the following cell parameters:

| Space group | Cell lengths/Å | Cell angles |
|---|---|---|
| P2$_1$ | a = 6.6629(6) | α = 90 |
| | b = 10.6505(15) | β = 98.136(10) |
| | c = 10.5671(11) | γ = 90 |

In some embodiments of the present invention, the crystalline Form 5 of Mavacamten, as defined according to any aspect or embodiment described herein, may exhibit plate-like morphology. Crystalline Form 5 having the morphology as described herein provides advantageous processing characteristics and/or stability due to particles having uniform morphology.

In a further embodiment, crystalline Form 5 of Mavacamten according to the present invention is a stable form; i.e., it does not display solid to solid phase transformation when exposed to high temperatures and high relative humidity.

Another aspect of the present invention relates to a process for preparing Form 5 of Mavacamten comprising:
  providing a solution of Mavacamten in an organic solvent, preferably a monocarboxylic acid or a monocarboxylic acid amide, particularly N,N-dimethylacetamide or acetic acid;
  optionally, heating up to reflux temperature; and
  crystallization of Form 5; optionally in the presence of an anti-solvent.

In another aspect of the present invention, there is provided a process for preparing a crystalline Form 5 of Mavacamten comprising providing a suspension of Mavacamten in an organic solvent, preferably an alkane, more preferably, a straight-chain alkane, particularly n-heptane, at elevated temperature and isolating Form 5 of Mavacamten.

The present disclosure comprises also a crystalline polymorph of Mavacamten, designated Form 6. The crystalline Form 6 of Mavacamten may be characterized by data selected from one or more of the following: an X-ray powder diffraction pattern substantially as depicted in FIG. 6; an X-ray powder diffraction pattern having peaks at 6.4, 9.3, 12.7, 13.3 and 20.8±0.2 degrees two-theta; and combinations of these data.

Form 6 of Mavacamten may be anhydrous.

The above crystalline polymorphs can be used to prepare other crystalline polymorphs of Mavacamten, Mavacamten salts and their solid state forms.

The present disclosure encompasses a process for preparing other solid state forms of Mavacamten, Mavacamten salts and their solid state forms thereof. The process for preparing salts of Mavacamten includes acidifying any one or a combination of the above described solid state forms of Mavacamten to obtain the corresponding salt.

The present disclosure also encompasses the use of crystalline polymorphs of Mavacamten of the present disclosure for the preparation of pharmaceutical compositions of crystalline polymorph Mavacamten and/or crystalline polymorphs thereof.

The present disclosure includes processes for preparing the above mentioned pharmaceutical compositions. The processes include combining any one or a combination of the crystalline polymorphs of Mavacamten of the present disclosure with at least one pharmaceutically acceptable excipient.

Pharmaceutical combinations or formulations of the present disclosure contain any one or a combination of the solid state forms of Mavacamten of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. CARBOPOL®), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Mavacamten and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

Mavacamten may be formulated for administration to a mammal, in embodiments to a human, by injection. Mavacamten can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Mavacamten and the pharmaceutical compositions and/or formulations of Mavacamten of the present disclosure can be used as medicaments, in embodiments in the treatment of obstructive hypertrophic cardiomyopathy (oHCM).

The present disclosure also provides methods of treating obstructive hypertrophic cardiomyopathy by administering a therapeutically effective amount of any one or a combination of the crystalline polymorphs of Mavacamten of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

Sample, after being powdered in a mortar and pestle, is applied directly on a silicon plate holder. The X-ray powder diffraction pattern was measured with Philips X'Pert PRO X-ray powder diffractometer, equipped with Cu irradiation source=1.54184 Å (Ångström), X'Celerator (2.022° 2θ) detector. Scanning parameters: angle range: 3-40 deg., step size 0.0167, time per step 37 s, continuous scan. The described peak positions were determined using silicon powder as an internal standard.

SEM Method:

SEM micrographs were taken on Joel JSM-5800 scanning microscope at 20 kV, WD 20-22, low current. Samples were sputtered with gold by Edwards S150 sputter coater.

Optical Microscope:

Samples were analyzed on Olympus BX53 optical microscope with camera Olympus XC50, using silicon oil as dispersion medium.

Single-Crystal X-Ray Diffraction ("SCXRD") Method

A suitable crystal was selected and mounted directly on the goniometer of Xcalibur, Sapphire3, Gemini diffractometer. The crystal was kept at 298 K during data collection. Data collection was carried out using CrysAlis Pro (Rigaku Oxford Diffraction). Using Olex2[1], the structure was solved with the SHELXT[2] structure solution program using Intrinsic Phasing and refined with the SHELXL[3] refinement package using Least Squares minimisation.

[1] Dolomanov, O. V., Bourhis, L. J., Gildea, R. J. Howard, J. A. K. & Puschmann, H. (2009), J. Appl. Cryst. 42, 339-341.
[2] Sheldrick, G. M. (2015), Acta Cryst. A71, 3-8.
[3] Sheldrick, G. M. (2015), Acta Cryst. C71, 3-8.

EXAMPLES

Preparation of Starting Materials

Mavacamten can be prepared according to methods known from the literature, for example U.S. Pat. No. 9,181,200 (Example 1).

Example 1: Preparation of Mavacamten Form 1

Mavacamten (50 mg) was dissolved in methanol (2 ml) at reflux temperature. Prepared solution was left open at room conditions for solvent to evaporate. After crystallization occurred, crystals were filtrated off and analyzed by XRPD. Form 1 of Mavacamten was obtained, as shown FIG. 1.

Example 2: Preparation of Mavacamten Form 2

Mavacamten (Form 1, 50 mg) was heated from 30° C. to 241° C. at 10° C./step and heating rate 10° C./min and then cooled to 30° C. The sample temperature was controlled using Anton Paar TCU100 Temperature Control Unit. Sample was analyzed by XRPD. Form 2 of Mavacamten was obtained, as shown in FIG. 2.

Example 3: Preparation of Mavacamten Amorphous

Mavacamten (2.0 grams) was dissolved in absolute ethanol (90 ml) by heating to 52° C. Prepared solution was then spray dried at following conditions: T(inlet)=100° C., Aspiration=35 m³h⁻¹ and Pump rate=6.9 ml/min. Obtained material was analyzed by XRPD. Amorphous was obtained, as shown in FIG. 3.

Example 4: Preparation of Mavacamten Form 4

Amorphous Mavacamten (20 mg) was exposed to atmosphere vapor of cyclohexane for 7 days. The obtained product was analyzed by XRPD. Form 4 of Mavacamten was obtained, as shown in FIG. 4.

Example 5: Preparation of Mavacamten Form 5

Amorphous Mavacamten (200 mg) was suspended in n-heptane (2 ml) at 40° C. for 4 hours and additionally stirred at 20-25° C. for 16 hours. Material was isolated by vacuum filtration and analyzed by XRPD. Form 5 of Mavacamten was obtained, as shown in FIG. 5.

Example 6: Preparation of Mavacamten Form 6

Amorphous Mavacamten (20 mg) was placed in an Eppendorf tube and the tube was placed in crystallization flask with 2 mL of chloroform. The crystallization flask was then closed. The sample was exposed to chloroform vapors for 14 days after which the material was analyzed by XRPD. Form 6 of Mavacamten was obtained, as shown in FIG. 6.

Example 7: Preparation of Mavacamten Form 1

Mavacamten (50 mg) was suspended in tetrahydrofuran (5 ml) at reflux temperature. Suspension was left open at room conditions for solvent to evaporate. After crystallization occurred, crystals were filtrated off and analyzed by XRPD-Form 1 of Mavacamten was obtained.

Example 8: Preparation of Mavacamten Form 5

Mavacamten (50 mg) was dissolved in N,N-dimethylacetamide (1 ml) at temperature of 100° C. Solution was left open at room conditions for solvent to evaporate. After crystallization occurred, crystals were filtrated off and analyzed by XRPD-Form 5 of Mavacamten was obtained.

Example 9: Preparation of Mavacamten Form 1

Mavacamten (1 gram) was dissolved in isobutanol (30 ml) at 80° C. Obtained solution was cooled to room temperature, stirred overnight and then additionally cooled (ice bath) for 1 hour. The obtained precipitate was filtrated off and analyzed by XRPD-Form 1 of Mavacamten.

Example 10: Preparation of Mavacamten Form 1

Mavacamten (50 mg) was dissolved in ethanol (2 ml) at 60° C. Solution was left open at room conditions for solvent to evaporate. After crystallization occurred, crystals were filtrated off and analyzed by XRPD-Form 1 of Mavacamten.

Example 11: Preparation of Mavacamten Form 5

Mavacamten (3 grams) was dissolved in acetic acid (25 ml) at 55° ° C. Obtained solution was cooled to room temperature and added dropwise into water (100 ml). Crystals were filtrated off and analyzed by XRPD-Form 5 of Mavacamten.

The invention claimed is:

1. A crystalline form of Mavacamten designated as Form 1, characterized by an X-ray powder diffraction pattern substantially as depicted in FIG. 1, wherein the peak at 28.48 belongs to silicon.

2. The crystalline Form 1 of Mavacamten according to claim 1; wherein the form is an anhydrous form.

3. The crystalline Form 1 of Mavacamten according to claim 1, which is further characterized by the following cell parameters:

| Space group | Cell lengths/Å | Cell angles |
|---|---|---|
| $P2_12_12_1$ | a = 9.444 (3) | α = 90 |
| | b = 12.1038(19) | β = 90 |
| | c = 12.664(2) | γ = 90. |

4. A pharmaceutical composition comprising the crystalline Form 1 of Mavacamten according to claim 1 and at least one pharmaceutically acceptable excipient.

5. A pharmaceutical composition comprising the crystalline Form 1 of Mavacamten according to claim 3 and at least one pharmaceutically acceptable excipient.

6. A process for preparing the pharmaceutical composition according to claim 4, comprising combining the crystalline Form 1 of Mavacamten with at least one pharmaceutically acceptable excipient.

7. A process for preparing the pharmaceutical composition according to claim 5, comprising combining the crystalline Form 1 of Mavacamten with at least one pharmaceutically acceptable excipient.

8. A medicament comprising the crystalline Form 1 of Mavacamten according to claim 1.

9. A medicament comprising the crystalline Form 1 of Mavacamten according to claim 3.

10. A method of treating obstructive hypertrophic cardiomyopathy (oHCM), comprising administering a therapeutically effective amount the crystalline Form 1 of Mavacamten according to claim 1 to a subject in need of the treatment.

11. A method of treating obstructive hypertrophic cardiomyopathy (oHCM), comprising administering a therapeutically effective amount the crystalline Form 1 of Mavacamten according to claim 3 to a subject in need of the treatment.

12. A process for preparing crystalline Form 1 of Mavacamten according to claim 1, comprising either:
providing Mavacamten in an alcohol or dimethylformamide;
heating up to reflux temperature; and
crystallizing Form 1 of Mavacamten either by solvent evaporation under room temperature conditions, or by cooling the solution to about 0° C.; or
providing a suspension of Mavacamten in an ether at reflux temperature; and
removing the solvent.

13. The process according to claim 12, wherein the alcohol is methanol, 2-butanol, isobutanol, or 1-propanol; and
the ether is a cyclic ether.

14. A process for preparing crystalline Form 1 of Mavacamten according to claim 3, comprising either:
providing Mavacamten in an alcohol or dimethylformamide;
heating up to reflux temperature; and
crystallizing Form 1 of Mavacamten either by solvent evaporation under room temperature conditions, or by cooling the solution to about 0° C.; or
providing a suspension of Mavacamten in an ether at reflux temperature; and
removing the solvent.

15. The process according to claim 14, wherein the alcohol is methanol, 2-butanol, isobutanol, or 1-propanol; and
the ether is a cyclic ether.

16. A crystalline form of Mavacamten designated as Form 5, characterized by an X-ray powder diffraction pattern having peaks at 13.4, 14.8, 21.8, 23.8 and 24.6 degrees 2-theta±0.2 degrees 2-theta.

17. The crystalline Form 5 of Mavacamten according to claim 16, characterized by an X-ray powder diffraction pattern having peaks at: 13.4, 14.8, 21.8, 23.8 and 24.6 degrees 2-theta±0.2 degrees 2-theta; and further characterized by having one, two, three or four additional peaks selected from 11.9, 15.8, 18.9 and 20.1 degrees 2-theta±0.2 degrees 2-theta.

18. The crystalline Form 5 of Mavacamten according to claim 17, characterized by an X-ray powder diffraction pattern having peaks at 11.9, 13.4, 14.8, 15.8, 18.9, 20.1, 21.8, 23.8 and 24.6 degrees 2-theta±0.2 degrees 2-theta.

19. The crystalline Form 5 of Mavacamten according to claim 16, characterized by the X-ray powder diffraction pattern substantially as depicted in FIG. 5.

20. The crystalline Form 5 of Mavacamten according to claim 16, wherein the form is an anhydrous form.

21. A pharmaceutical composition comprising the crystalline Form 5 of Mavacamten according to claim 16 and at least one pharmaceutically acceptable excipient.

22. A process for preparing the pharmaceutical composition according to claim 21, comprising combining the crystalline Form 5 of Mavacamten with at least one pharmaceutically acceptable excipient.

23. A medicament comprising the crystalline Form 5 of Mavacamten according to claim 16.

24. A method of treating obstructive hypertrophic cardiomyopathy (oHCM), comprising administering a therapeutically effective amount the crystalline Form 5 of Mavacamten according to claim 16 to a subject in need of the treatment.

* * * * *